(12) United States Patent
Hsiao

(10) Patent No.: US 9,144,591 B2
(45) Date of Patent: *Sep. 29, 2015

(54) TRANSCRIPTION MODULATOR COMPOSITIONS

(71) Applicant: Academia Sinica, Taipei (TW)

(72) Inventor: Pei-Wen Hsiao, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/055,545

(22) Filed: Oct. 16, 2013

(65) Prior Publication Data

US 2014/0141109 A1 May 22, 2014

Related U.S. Application Data

(63) Continuation of application No. 11/386,985, filed on Mar. 21, 2006, now Pat. No. 8,597,701.

(51) Int. Cl.
*A61K 36/28* (2006.01)

(52) U.S. Cl.
CPC .................................. *A61K 36/28* (2013.01)

(58) Field of Classification Search
None
See application file for complete search history.

(56) References Cited

U.S. PATENT DOCUMENTS

| | | | |
|---|---|---|---|
| 5,130,133 A * | 7/1992 | Rajagopalan et al. ........ | 424/736 |
| 5,559,146 A | 9/1996 | Sablon | |
| 6,117,429 A | 9/2000 | Bucci | |
| 2002/0192310 A1 | 12/2002 | Bland et al. | |
| 2005/0032882 A1 | 2/2005 | Chen | |

FOREIGN PATENT DOCUMENTS

| | | | |
|---|---|---|---|
| JP | 11012134 A | | 1/1999 |
| JP | 11012134 A | * | 1/1999 |
| JP | 2000344630 A | | 12/2000 |

OTHER PUBLICATIONS

Kim et al. "Effects of 2, 4-D and DCP on the DHT-induced androgenic action in human prostate cancer cells" Toxicol. Sci. 88(1):52-59 (2005).
Wilson et al. "A novel cell line, MDA-kb2, that stably expresses an androgen and glucocorticoid-responsive reporter for the detection of hormone receptor agonists and antagonists" Toxicol. Sci. 66(1):69-81 (2002).
Wilson et al. "Development and characterization of a cell line that stably expresses an estrogen-responsive luciferase reporter for the detection of estrogen receptor agonist and antagonists" Toxicol. Sci. 81(1):69-77 (2004).
K. B. J.M. Cleutjens et al. "An Androgen Response Element in a Far Upstream Enhancer Region is Essential for High, Androgen-Regulated Activity of the Prostate-Specific Antigen Promoter". Molecular Endocrinology 11: 148-161, 1997.
Y. T. Kwak et al. "Analysis of Domains in the IKK-alpha and IKK-beta Proteins That Regulate Their Kinase Activity". The Journal of Biological Chemistry 275(19): 14752-14759, 2000.
M. Kobori et al. "Wedelolactone suppresses LPS-induced caspase-11 expression by directly inhibiting the IKK complex". Cell Death and Differentiation 11: 123-130, 2004.
M. Marcelli et al. "Altered growth and insulin-like-growth factor-binding protein-3 production in PC3 prostate carcinoma cells stably transfected with a constitutively active androgen receptor complementary deoxyriboncucleic acid". Endocrinolog:v 136(3):1040-1048, 1995.
J. A Simental et al. "Transcriptional activation and nuclear targeting signals of the human androgen receptor". The Journal of Biological Chemistry 266(1):510-518, 1991.
C. H. Regnier et al. "Identification and characterization of an IKB kinase". Cell 90:3 73-383, 1997.
L. Ling et al. "NF-kB-inducing kinase activities IKK-alpha by phosphorylation of Ser-176". Proc. Natl. Acad. Sci. USA 95:3792-3797, Mar. 1998.
R. Butler et al. "Nonapoptotic cell death associated with s-phase arrest of prostate cancer cells via the peroxisome proliferators-activated receptor γ". Cell Growth and Differentiation 11:49-61, Jan. 2000.
Y. Cao et al. "IKK-alpha provides an essential link between RANK signaling and cyclin DI expression during mammary gland development". Cell 107:763-775, Dec. 2001.
M. Karin et al. "NF-kB in Cancer: From innocent bystander to major culprit". Nature Reviews:2:301-310, Apr. 2002.
N. Kishore et al. "A selective IK.K.-2 inhibitor blocks NF-kB-dependent gene expression in AT interleukin-1-beta-stimulated synovial fibroblasts". The Journal of Biological Chemistry 278(35):32861-32871, 2003.
A Hartel et al. "Characterization of steroid receptor expression in human prostate carcinoma cell line 22RV1 and quantification of androgen effects on mRNA regulation of prostate-specific genes". Journal of Steroid Biochemistry & Molecular Biology 92:187-197, 2004.
V. Anest et al. "A nucleosomal function for IkB kinase-alpha in NF-kB-dependent gene expression". Nature 423:659-683, Jun. 2003.
C. D. Chen et al. "Molecular determinants of resistance to anti-androgen therapy". Nature Medicine 10(1):33-39, Jan. 2004.
L. Cheng et al. "CWR22 Xenograft as an ex vivo human tumor model for prostate cancer gene therapy". Journal of the National Cancer Institute 88(9):607-611, May 1996.
B. J. Feldman et al. "The development of androgen-independent prostate cancer". Nature 1 :34-45, Oct. 2001.
J. Hisatake et al. "Down-regulation of prostate-specific antigen expression by Ligands for peroxisome proliferation activated receptor γ". Cancer Research 60:5494-5498, Oct. 2000.

(Continued)

*Primary Examiner* — Terry A McKelvey
*Assistant Examiner* — Catheryne Chen
(74) *Attorney, Agent, or Firm* — Cesari and McKenna, LLP

(57) ABSTRACT

Disclosed herein is a method for treating an androgen-stimulated disease in a subject in need thereof by administering to the subject a composition containing an effective amount of an inhibitor of IκB kinase subunit α activity. The composition can also be administered to a subject at high risk for prostate cancer as a method for reducing the subject's risk thereof. A further method relates to identifying a modulator of transcriptional activity regulated by IκB kinase subunit α. Still another method relates to determining the IκB kinase subunit α-regulated transcriptional activity regulated by in a non-human mammalian test subject.

3 Claims, No Drawings

(56) References Cited

OTHER PUBLICATIONS

W. Huang et al. "Cooperative assembly of androgen receptor into a nucleoprotein complex that regulates the prostate-specific antigen enhancer". The Journal of Biological Chemistry 274(36):25756-25768, 1999.
Q. Li et al. "Severe liver degeneration in mice lacking the IkB kinase 2 gene". Science 284:32i-325, Apr. 1999.
S. McDonald et al. "Ligand responsiveness in human prostate cancer: structural analysis of mutant androgen receptors from LNCaP and CWR22 tumors". Cancer Research 60:2317-2322, May 2000.
M. Nagabhushan et al. "CWR22: the first human prostate cancer xenograft with strongly androgen-dependent and relapsed strains both in vivo and in soft agar" (abstract only). Cancer Research 56(13):3042-3046, 1996.
K.-J. Park et al. "Formation of an IK.K-alpha-dependent transcription complex is required for estrogen receptor-mediated gene activation". Molecular Cell 18:71-82, Apr. 2005.
T. J. Polascik et al. "Prostate specific antigen: a decade of discovery what we have learned and where we are going". The Journal of Urology 162:293-306, Aug. 1999.
T. G. Pretlow et al. "Xenografts of primary human prostatic carcinoma" (abstract only). J. Natl.Cancer Inst. 85(5):394-398, Mar. 1993.
R. W. Ross et al. "Osteoporosis in men treated with androgen deprivation therapy for prostate cancer". The Journal of Urology 167:1952-1956, May 2002.
A. Rossi et al. "Anti-inflammatory cyclopentanone prostaglandins are direct inhibitors of IkB kinase". Nature 403: 103-108, Jan. 2000.
T. S. Shao et al. "In vivo preservation of steroid specificity in CWR22 xenografts having a mutated androgen receptor". The Prostate 57: 1-7, 2003.
R. M. Stramkoski et al. "A new human prostate carcinoma cell line" (abstract only). In Vitro Cell Dev Biol Anim. 35(7):403-409, Jul.-Aug. 1999.
G. Takaesu et al. "TAK1 is critical for IkB kinase-mediated activation of the NF-kB pathway". J. Mol. Bio. 326:105-115, 2003.
J. Trachtenberg. "A review of hormonal treatment in advanced prostate cancer" (abstract only). CanJ. Urol. 4(2 Supp. 1):61-64, Jun. 1997.
M. Van De Wetering et al. "Specific inhibition of gene expression using a stably integrated, inducible small-interfering-RNA vector". EMBO Reports 4(6):609-615, 2003.
T. Visakorpi et al. "In vivo amplification of the androgen receptor gene and progression of human prostate cancer" (abstract only). Nat Genet. 9(4):401-406, Apr. 1995.
M.A. Wainstein et al. "CWR22: androgen- dependent xenograft model derived from a primary human prostatic carcinoma" (abstract only). Cancer Res. 54(23):6049-6052, Dec. 1994.
Y. Yamamoto et al. "IkB kinases: key regulators of the NF-kB pathway". Trends in Biochemical Sciences 29(2):72-79, Feb. 2004.
Y. Yamamoto et al. "Histone H3 phosphorylation by IKK-alpha is critical for cytokine-induced gene expression". Nature 423:655-659, Jun. 2003.
O. L. Zegarra-Moro et al. "Disruption of androgen receptor function inhibits proliferation of androgen-refractory prostate cancer cells". Cancer Research 62: 1008-1013, Feb. 2002.
L. Famana et al. "Apoptosis induction by a novel retinoid-related molecule requires nuclear factorkB activation". Cancer Res. 65(11):4909-4917, Jun. 2005.
C. Xu et al. "Suppression of NF-kB and MF-kB-regulated gene expression by sulforaphane and PEITC through IkB-alpha, IKK pathways in human prostate cancer PC-3 cells". Oncogene 24:4486-4495, 2005.
M. G. Jayathirtha et al. "Optimization of wedelolactone accumulation in shoot cultures of eclipta alba" (abstract only). Indian J. Exp. Biol. 41(12):1476-1478, Dec. 2003.
M. G. Jayathirtha et al. "Preliminary immunomodulatory activities of methanol extracts of eclipta alba and centella asiatica" (abstract only). Phytomedicine 11(4):361-365, 2004.
S. Shukla et al. "Suppression of constitutive and tumor necrosis factor alpha-induced nuclear factor (NF)-kB activation and induction of apoptosis by apigenin in human prostate carcinoma . . . " Clinical Cancer Research 10:3169-3178, May 2004.
C. C. Li et al. "Total synthesis of wedelolactone". J. Org. Chem 68:8500-8504, 2003.
S. Dhanalakshmi et al. "Inhibition ofNF-kappaB pathway in grape seed extract-induced apoptotic death of human prostate carcinoma DU145 cells" (abstract only). Int. J. Oncol. 23(3):721-727, Sep. 2003.
S. D. Syed et al. "Trypsin inhibitory effect of wedelolactone and demethylwedelolactone". Phytotherapy Research 17:420-421, 2003.
J. S. Zhang et al. "Studies on the chemical constituents of eclipta prostrate (L)" (abstract only). Yao Xue Xue Bao 36(1):34-37, Jan. 2001.
S. Dhanalakshmi et al. "Silibinin inhibits constitutive and TNF-alpha-induced activation of NF-kB and sensitizes human prostate carcinoma DU145 cells to TNF-alpha-induced apoptosis". Oncogene 21:1759-1767, 2002.
B. Singh et al. "In vivo hepatoprotective activity of active fraction from ethanolic extract of eclipta alba leaves". Indian J. Physiol. Pharmacol. 45(4):435-441, Oct. 2001.
A. V. Gasparian et al. "The role of IKK in constitutive activation of NF-kB transcription factor in prostate carcinoma cells". Journal of Cell Science 115: 114-151, 2002.
Demirturk et al., In-vitro-In vivo Correlations, 2003, FABAD J Pharm Sci, 28: 215-224.
2011 http://www.fpnotebook.com/gyn/Endo/Hyprndrgnsm.htm.
Feb. 2005 http://www.medicinenet.com/scripUmain/art.asp?articlekey=52164.
Thornton et al., Effects of Androgens on the Growth of Cultured Human Dermal Papilla Cells Derived from Beard and Scalp Hair Follicles, 1991, J Invest Dermatol, 97: 345-348.
Wedelia date: Oct. 16, 2001 http://www.hulu.com.tw/moi/Wedelia_1 M.htm.
An et al., Drug Interactions between the Proteosome Inhibitor Bortezomib and Cytotoxic Chemotherapy, Tumor Necrosis Factor (TNF) alpha, and TNF-Related Apoptosis-Inducing Ligand in Prostate Cancer, 2003, Clinical Cancer Research, 9: 4537-4545.
Peet et al., IkB Kinases alpha and beta Show a Random Sequential Kinetic Mechanism and are Inhibited by Stauropsorine and Quercetin, 1999, JBC, 274: 32655-3266.
Cinar et al., Identification of a negative regulatory cis-element in the enhancer core region of the prostate-specific antigen promoter: implications for intersection of androgen receptor and nuclear factor-kappa B signaling in prostate cancer cells, 2004, Biochem. J., vol. 379, pp. 421-431.
Ghafar et al., Regression of Prostate Cancer Following Administration of Genistein Combined Polysaccharide (GCP tm), a Nutritional Supplement: A Case Report, 2002, J. Alternative and Complementary Medicine, vol. 8, pp. 493-497.
Davis et al., Genistein Inhibits NF-kB Activation in Prostate Cancer Cells, 1999, Nutrition and Cancer, vol. 35(2), pp. 167-174.

* cited by examiner

```
                              SEQUENCE LISTING

<160> NUMBER OF SEQ ID NOS: 6

<210> SEQ ID NO 1
<211> LENGTH: 15
<212> TYPE: DNA
<213> ORGANISM: Homo sapiens

<400> SEQUENCE: 1
agaacagcaa gtgct                                                         15

<210> SEQ ID NO 2
<211> LENGTH: 15
<212> TYPE: DNA
<213> ORGANISM: Homo sapiens

<400> SEQUENCE: 2
ggatcaggga gtctc                                                         15

<210> SEQ ID NO 3
<211> LENGTH: 15
<212> TYPE: DNA
<213> ORGANISM: Homo sapiens

<400> SEQUENCE: 3
ggaacatatt gtatc                                                         15

<210> SEQ ID NO 4
<211> LENGTH: 5763
<212> TYPE: DNA
<213> ORGANISM: Homo sapiens

<400> SEQUENCE: 4
agcttctagt tttcttttcc cggtgacatc gtggaaagca ctagcatctc taagcaatga        60
tctgtgacaa tattcacagt gtattgccat ccagggaact caactgagcc ttgatgtcca       120 gagattttg  tgttttttc  tgagactgag tctcgctctg tgcccaggct ggagtgcagt       180
ggtgcaacct tggctcactg caagctccgc ctcctgggtt cacgccattc tcctgcctca       240
gcctcctgag tagctgggac tacaggcacc cgccaccacg cctggctaat ttttttgtat       300
ttttagtaga gatggggttt cactgtgtta gccaggatgg tctcagtctc ctgacctcgt       360
gatctgccca ccttggcctc ccaaagtgct gggattacag gcgtgagcca ctgcgcctgg       420
ccgatatcca gagattttt  gggggctcc  atcacacaga catgttgact gtcttcatgg       480 ttgacttta  gtatccagcc cctctagaaa tctagctgat atagtgtggc tcaaaacctt       540
cagcacaaat cacaccgtta gactatctgg tgtggcccaa accttcaggt gaacaaaggc       600
actctaaact ggcaggatat tccaaagcat tagagatgac ctcttgcaaa gaaaaagaaa       660
tggaaaagaa aaagaaagaa aggaaaaaaa aaaaaaaaaa gagatgacct ctcaggctct       720
gaggggaaac gcctgaggtc tttgagcaag gtcagtcctc tgttgcacag tctccctcac       780
agggtcattg tgacgatcaa atgtggtcac gtgtatgagg caccagcaca tgcctggctc       840
tggggagtgc cgtgtaagtg tatgcttgca ctgctgaatg gctgggatgt gtcagggatt       900
atcttcagca cttacagatg ctcatctcat cctcacagca tcactatggg atgggtatta       960
ctggcctcat ttgatggaga aactggctgt ggctcagaaa gggggggacca ctagaccagg     1020
```

```
gacactctgg atgctgggga ctccagagac catgaccact caccaactgc agagaaatta    1080
attgtggcct gatgtccctg tcctggagag ggtggaggtg gaccttcact aacctcctac    1140
cttgaccctc tcttttaggg ctctttctga cctccaccat gatactagga ccccattgta    1200
ttctgtaccc tcttgactct atgaccccca ctgcccactg catccagctg ggtcccctcc    1260
tatctctatt cccagctggc cagtgcagtc tcagtgccca cctgtttgtc agtaactctg    1320
aaggggctga cattttactg acttgcaaac aaataagcta actttccaga gttttgtgaa    1380
tgctggcaga gtccatgaga ctcctgagtc agaggcaaag gcttttactg ctcacagctt    1440
agcagacagc atgaggttca tgttcacatt agtacacctt gcccccccca aatcttgtag    1500
ggtgaccaga gcagtctagg tggatgctgt gcacacgggg tttgtgccac tggtgagaaa    1560
cctgagatta ggaatcctca atcttatact gggacaactt gcaaacctgc tcagcctttg    1620
tctctgatga agatattatc ttcatgatct tggattgaaa acagacctac tctggaggaa    1680
catattgtat cgattgtcct tgacagtaaa caaatctgtt gtaagagaca ttatctttat    1740
tatctaggac agtaagcaag cctggatctg agagagatat catcttgcaa ggatgcctgc    1800
tttacaaaca tccttgaaac aacaatccag aaaaaaaaag gtgttgctgt ctttgctcag    1860
aagacacaca gatacgtgac agaaccatgg agaattgcct cccaacactg ttcagccaga    1920
gccttccacc cttgtctgca ggacagtctc aacgttccac cattaaatac ttcttctgtc    1980
acatcctgct tatttatgcc taaccaaggt tctaggtccc gatcgactgt gtctggcagc    2040
actccactgc caaacccaga ataaggcagc gctcaggatc ccgaaggggc atggctgggg    2100
atcagaactt ctgggtttga gtgaggagtg ggtccaccct cttgaatttc aaaggaggaa    2160
gaggctggat gtgaaggaac tggggagggg aaagtgtcag ttccgaactc ttaggtcaat    2220
gagggaggag actggtaagg tcccagctcc cgaggtactg atgtgggaat ggcctaagaa    2280
tctcatatcc tcaggaagaa ggtgctggaa tcctgagggg tagagttctg ggtatatttg    2340
tggcttaagg ctcttttggcc cctgaaggc agaggctgga accattaggt ccagggtttg    2400
gggtgatagt aatgggatct cttgattcct caagagtctg aggatcgagg gttgcccatt    2460
cttccatctt gccacctaat ccttactcca cttgagggta tcaccagccc ttctagctcc    2520
atgaaggtgc ccctgggcaa gcacaatctg agcatgaaag atgccccaga ggccttgggt    2580
gtcatccact catcatccag catccacact ctgagggtgt ggccagcacc atgacgtcat    2640
gttgctgtga ctatccctgc agcgtgcctc tccagccacc tgccaaccgt agagctgccg    2700
acatcctcct ctggtgggag tggcctgcat ggtgccaggc tgaggcctag tgtcagacag    2760
ggagcctgga atcatagggga tccaggactc aaaagtgcta gagaatggcc atatgtcacc    2820
atccatgaaa tctcaaggc ttctgggtgg agggcacagg gacctgaact tatgggtttt    2880
ccccaagtct attgctctcc caagtgagtc tcccagatac gaggcactgt gccagcatca    2940
gccttatctc caccacatct tgtaaaaggg actaccaggg gccctgatga acaccatggt    3000
gtgtacagga gtaggggtg gaggcacgga ctcctgtgag gtcacagcca agggagcatc    3060
atcatgggtg gggaggaggc aatggacagg cttgagaacg gggatgtggt tgtatttggt    3120 tttcttggt tagataaagt gctgggtata ggattgagag tggagtatga agaccagtta    3180
ggatggagga tcagattgga gttgggttag agatgggta aaattgtgct tcggatgagt    3240
ttgggattga cactgtggag gtggtttggg atggcatggc tttgggatgg aaatagattt    3300
gttttgatgt tggctcagac atccttgggg attgaactgg ggatgaagct gggtttgatt    3360
```

```
ttggaggtag aagacgtgga agtagctgtc agatttgaca gtggccatga gttttgtttg    3420
atggggaatc aaacaatggg ggaagacata agggttggct tgttaggtta agttgcgttg    3480
ggttgatggg gtcggggctg tgtataatgc agttggattg gtttgtatta aattgggttg    3540
ggtcaggttt tggttgagga tgagttgagg atatgcttgg ggacaccgga tccatgaggt    3600
tctcactgga gtggagacaa acttcctttc caggatgaat ccggggaagc cttaattcac    3660
gtgtagggga ggtcaggcca ctggctaagt atatccttcc actccagctc taagatggtc    3720
ttaaattgtg attatctata tccacctctg tctccctcac tgtgcttgga gtttacctga    3780
tcactcaact agaaacaggg gaagatttta tcaaattctt ttttttttt tttttttttt    3840
tgagacagag tctcactctg ttgcccaggc tggagtgcag tggcgcagtc tcggctcact    3900
gcaacctctg cctcccaggt tcaagtgatt ctcctgcctc agcctcctga gttgctggga    3960
ttacaggcat gcagcaccat gcccagctaa ttttttgtatt tttagtagag atggggtttc    4020
accaatgttt gccaggctgg cctcgaactc ctgacctggt gatccacctg cctcagcctc    4080
ccaaagtgct gggattacag gcgtcagcca ccgcgcccag ccacttttgt caaattcttg    4140
agacacagct cgggctggat caagtgagct actctggttt tattgaacag ctgaaataac    4200
caactttttg gaaattgatg aaatcttacg gagttaacag tggaggtacc agggctctta    4260
agagttcccg attctcttct gagactacaa attgtgattt tgcatgccac cttaatcttt    4320
tttttttttt ttttaaatcg aggtttcagt ctcattctat ttcccaggct ggagttcaat    4380
ggcgtgatca cagctcactg tagccttgaa ctcctggcct taagagattc tcctgcttcg    4440
gtctcccaat agctaagact acagtagtcc accaccatat ccagataatt tttaaatttt    4500
ttggggggcc gggcacagtg gctcacgcct gtaatcccaa caccatggga ggctgagatg    4560
ggtggatcac gaggtcagga gtttgagacc agcctgacca acatggtgaa actctgtctc    4620
tactaaaaaa aaaaaaaata gaaaaattag ccgggcgtgg tggcacacgg cacctgtaat    4680
cccagctact gaggaggctg aggcaggaga atcacttgaa cccagaaggc agaggttgca    4740
atgagccgag attgcgccac tgcactccag cctgggtgac agagtgagac tctgtctcaa    4800
aaaaaaaaaa tttttttttt tttttgtag agatggatct tgctttgttt ctctggttgg    4860
ccttgaactc ctggcttcaa gtgatcctcc taccttggcc tcggaaagtg ttgggattac    4920
aggcgtgagc caccatgact gacctgtcgt ttaatcttga ggtacataaa cctggctcct    4980
aaaggctaaa tattttgttg gagaaggggc attggatttt gcatgaggat gattctgacc    5040
tgggagggca ggtcagcagg catctctgtt gcacagatag agtgcacagg tctgagaac     5100
aaggagtggg gggttattgg aattccacat tgtttgctgc acgttggatt ttgaaatgct    5160
agggaacttt gggagactca tatttctggg ctagaggatc tgtggaccac aagatctttt    5220
tatgatgaca gtagcaatgt atctgtggag ctggattctg ggttgggagt gcaaggaaaa    5280
gaatgtacta aatgccaaga catctatttc aggagcatga ggaataaaag ttctagtttc    5340
tggtctcaga gtggtgcagg gatcagggag tctcacaatc tcctgagtgc tggtgtctta    5400
gggcacactg ggtcttggag tgcaaaggat ctaggcacgt gaggctttgt atgaagaatc    5460
ggggatcgta cccacccct gtttctgttt catcctgggc gtgtctcctc tgcctttgtc     5520
ccctagatga agtctccatg agctacaggg cctggtgcat ccagggtgat ctagtaattg    5580
cagaacagca agtgctagct ctccctcccc ttccacagct ctgggtgtgg gaggggttg     5640
tccagcctcc agcagcatgg ggagggcctt ggtcagcctc tgggtgccag cagggcaggg    5700
gcggagtcct ggggaatgaa ggttttatag ggctcctggg ggaggctccc cagccccaag    5760
```

```
ctt                                                                  5763

<210> SEQ ID NO 5
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 5
gcaggcucuu ucagggaca                                                   19

<210> SEQ ID NO 6
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 6
ggugaagagg ugguggugag c                                                21
```

TRANSCRIPTION MODULATOR COMPOSITIONS

CROSS REFERENCE TO RELATED APPLICATION

This application is a continuation of U.S. application Ser. No. 11/386,985, filed on Mar. 21, 2006, the content of which is incorporated herein by reference in its entirety.

BACKGROUND

Androgens define a broad class of steroid hormones that control primarily the development and maintenance of male characteristics. They exert their physiological effects through the androgen receptor (AR), a member of the steroid hormone nuclear receptor superfamily. The AR is activated by binding an androgen (e.g., testosterone) or a related ligand. Activated AR triggers a signal transduction pathway that drives increased transcription of a number of "androgen-responsive" target genes, e.g., prostate specific antigen (PSA). Of note, the signal transduction steps in this pathway have not been fully elucidated.

AR activation by androgens, followed by increased androgen-responsive target gene transcription, stimulates a number of diseases, e.g., prostate cancer. Thus, treating prostate cancer usually includes administering an AR antagonist. Unfortunately, its effectiveness is frequently short-lived, as the AR expressed by cancer cells often becomes androgen-independent, i.e., constitutively active (e.g., due to a mutation). Consequently, the ligand-independent AR drives a high level of target gene transcription that supports persistent cancer growth even in the presence of an AR antagonist.

Thus, there is a need for compositions that modulate androgen-responsive target gene transcription at a signal transduction step downstream of AR activation, as well as methods for their identification and therapeutic use.

SUMMARY

The present invention is based, in part, on the unexpected findings that IκB kinase subunit α (IKKα) interacts with AR and that its activity is critical to androgen-responsive gene transcription.

Accordingly, one aspect of the invention relates to a method for treating an androgen-stimulated disease by administering to a subject a composition containing an effective amount of an inhibitor of IKKα activity. Preferably, prior to administration of the composition, the subject is diagnosed as having the androgen-stimulated disease. An androgen-stimulated disease is any abnormal health condition that is caused by or worsened by AR activity, e.g., prostate cancer, benign prostate hypertrophy, breast cancer, male alopecia, propionibacterium acne, polycystic ovarian syndrome, autosomal dominant polycystic kidney disease, or hyperandrogenism. The composition can contain an extract from *Wedelia chinensis, Eclipta prostrata*, or *Eclipta alba*. The inhibitor of IKKα activity can be wedelolactone, luteolin, quercetin, apigenin, 15-deoxy-$\Delta^{12,14}$-prostaglandin $J_2$, or prostaglandin A1. The method can also include determining a PSA level in a biological sample from the subject before or after administration of the above composition to the subject. Determining a PSA level before the administration is useful for diagnosing the subject as having an androgen-stimulated disease, e.g., prostate cancer. The PSA level determined after administration is a reliable index of the therapeutic response to the above-described method for treating an androgen-stimulated disease.

A further aspect of the invention relates to a method for reducing the risk of prostate cancer in a high risk subject by administering to the subject a composition containing an effective amount of an inhibitor of IKKα activity.

Another aspect of the invention relates to a method for identifying a modulator, i.e., an inhibitor or stimulator of IKKα-regulated transcriptional activity. Inhibitors of the transcriptional activity are useful for, e.g., treating androgen-stimulated diseases such as prostate cancer. The method includes (1) providing a mammalian cell that expresses IKKα and AR, and contains an isolated nucleic acid including the sequence of an androgen-responsive promoter operably linked to a sequence encoding a reporter polypeptide so that the cell also expresses the reporter polypeptide, (2) contacting the cell with a test composition, and (3) assaying an expression level (i.e., of mRNA or protein) or an activity of the reporter polypeptide. If the test composition increases or decreases the expression level or activity of the encoded reporter polypeptide relative to a negative control treatment, it is considered a modulator of transcriptional activity regulated by IKKα. The expressed AR can be a constitutively active mutant. If the AR is not constitutively active, the method includes contacting the cell with an AR agonist. The method can also include determining the effect of a test composition on IKKα activity to further characterize the mechanism by which the test composition modulates transcriptional activity regulated by this kinase.

Still another aspect of the invention relates to a method for determining transcriptional activity regulated by IKKα in a non-human mammalian test subject. The method is useful for, e.g., determining the efficacy of a candidate IKKα inhibitor composition in vivo. It includes (1) introducing a number of cells expressing IKKα and androgen receptor, and containing an isolated nucleic acid having the sequence of an androgen-responsive promoter operably linked to a sequence encoding a reporter polypeptide so that the cell also expresses the reporter polypeptide; and (3) detecting an activity of the reporter polypeptide expressed by the cells. Detection of the reporter activity (e.g., in vivo) indicates transcriptional activity regulated by IKKα in the test subject. The method can also include determining a level of the IKKα activity in a biological sample from the test subject.

Other features or advantages of the present invention will be apparent from the following detailed description, and also from the claims.

DETAILED DESCRIPTION

Methods are described below for identifying compositions that specifically modulate IKKα-regulated transcription (IKKαRT), e.g., transcription of androgen-responsive target genes. Also described below are methods for treating a subject suffering from, or at high risk for, an androgen-stimulated disease by administering an effective amount of such compositions.

IKKαRT modulator compositions (i.e., compositions that either decrease or increase IKKαRT) are identified by an androgen-responsive reporter assay.

An androgen-responsive reporter construct is generated by fusing an androgen-responsive promoter to a nucleic acid encoding a reporter polypeptide. An androgen-responsive promoter is a promoter that can be activated by an AR-dependent signaling pathway. The androgen-responsive reporter construct is introduced into a host cell to generate an androgen-responsive reporter cell in which the androgen-responsive promoter drives expression of the reporter polypeptide. To assess the ability of a test composition to modulate IKKαRT in the reporter cells, IKKα activity of reporter cells can be increased by contacting the cells with an androgen (e.g., testosterone or 5α-dihydrotestosterone) in the presence or absence of the test composition. After contacting the cells with the androgen plus or minus the test composition, reporter expression or activity is assayed. If the expression or activity of the reporter, in response to androgen stimulation, is increased or decreased in the presence of the test composition versus its absence, the composition is considered an IKKαRT modulator.

A test composition can be, e.g., a naturally occurring composition purified from a biological source or synthesized, a plant extract, a protein, a peptide, or a small molecule (e.g., a compound selected from a combinatorial synthesis library).

Suitable androgen-responsive reporter cells can be derived from mammalian tissues or cell lines (e.g., from human, monkey, mouse, rat, or hamster). The host cells endogenously or heterologously express IKKα (e.g., GenBank No. NP_001269 and the AR (e.g., GenBank No. AAA51729). For example, the human PCa 22Rv1 cell line, available from the American Type Culture Collection (ATCC® Number: CRL-2505™) can be used to generate an androgen-responsive reporter cell line.

In the reporter assay, androgen stimulation can be avoided by using reporter cells that express a constitutively active AR, e.g., as in Marcelli et al. (1995), *Endocrinology* Vol. 136, No. 3.

Methods for generating reporter constructs, introducing them into cells, and assaying various reporter polypeptide activities, can be found in detail in, e.g., *Current Protocols in Molecular Biology*, John Wiley & Sons, N.Y. (2005), 3.16-3.17 and 9.1-9.14, respectively).

The androgen-responsive promoter should include at least one of the following androgen responsive elements:

```
AGAACAGCAAGTGCT    (SEQ ID NO: 1)
GGATCAGGGAGTCTC    (SEQ ID NO: 2)
GGAACATATTGTATC    (SEQ ID NO: 3)
```

See Cleutjens et al. (1997), *Mol. Endocrinol.* 11(9):1256-65.

For example, the androgen-responsive promoter can be a PSA promoter, which contains all three of the above-listed androgen-responsive elements, and has the following sequence:

```
                                        (SEQ ID NO: 4)
AGCTTCTAGTTTTCTTTTCCCGGTGACATCGTGGAAAGCACTAGCATCTC

TAAGCAATGATCTGTGACAATATTCACAGTGTATTGCCATCCAGGGAACT

CAACTGAGCCTTGATGTCCAGAGATTTTTGTGTTTTTTCTGAGACTGAG

TCTCGCTCTGTGCCCAGGCTGGAGTGCAGTGGTGCAACCTTGGCTCACTG

CAAGCTCCGCCTCCTGGGTTCACGCCATTCTCCTGCCTCAGCCTCCTGAG

TAGCTGGGACTACAGGCACCCGCCACCACGCCTGGCTAATTTTTTGTAT

TTTTAGTAGAGATGGGGTTTCACTGTGTTAGCCAGGATGGTCTCAGTCTC

CTGACCTCGTGATCTGCCCACCTTGGCCTCCCAAAGTGCTGGGATTACAG

GCGTGAGCCACTGCGCCTGGCCGATATCCAGAGATTTTTTGGGGGCTCC

ATCACACAGACATGTTGACTGTCTTCATGGTTGACTTTTAGTATCCAGCC

CCTCTAGAAATCTAGCTGATATAGTGTGGCTCAAAACCTTCAGCACAAAT

CACACCGTTAGACTATCTGGTGTGGCCCAAACCTTCAGGTGAACAAAGGC

ACTCTAAACTGGCAGGATATTCCAAAGCATTAGAGATGACCTCTTGCAAA

GAAAAAGAAATGGAAAAGAAAAAGAAAGAAAGGAAAAAAAAAAAAAAAAA

GAGATGACCTCTCAGGCTCTGAGGGGAAACGCCTGAGGTCTTTGAGCAAG

GTCAGTCCTCTGTTGCACAGTCTCCCTCACAGGGTCATTGTGACGATCAA

ATGTGGTCACGTGTATGAGGCACCAGCACATGCCTGGCTCTGGGGAGTGC

CGTGTAAGTGTATGCTTGCACTGCTGAATGGCTGGGATGTGTCAGGGATT

ATCTTCAGCACTTACAGATGCTCATCTCATCCTCACAGCATCACTATGGG

ATGGGTATTACTGGCCTCATTTGATGGAGAAACTGGCTGTGGCTCAGAAA

GGGGGGACCACTAGACCAGGGACACTCTGGATGCTGGGGACTCCAGAGAC

CATGACCACTCACCAACTGCAGAGAAATTAATTGTGGCCTGATGTCCCTG

TCCTGGAGAGGGTGGAGGTGGACCTTCACTAACCTCCTACCTTGACCCTC

TCTTTTAGGGCTCTTTCTGACCTCCACCATGATACTAGGACCCCATTGTA

TTCTGTACCCTCTTGACTCTATGACCCCCACTGCCCACTGCATCCAGCTG

GGTCCCCTCCTATCTCTATTCCCAGCTGGCCAGTGCAGTCTCAGTGCCCA

CCTGTTTGTCAGTAACTCTGAAGGGGCTGACATTTTACTGACTTGCAAAC

AAATAAGCTAACTTTCCAGAGTTTTGTGAATGCTGGCAGAGTCCATGAGA

CTCCTGAGTCAGAGGCAAAGGCTTTTACTGCTCACAGCTTAGCAGACAGC

ATGAGGTTCATGTTCACATTAGTACACCTTGCCCCCCCCAAATCTTGTAG

GGTGACCAGAGCAGTCTAGGTGGATGCTGTGCACACGGGGTTTGTGCCAC

TGGTGAGAAACCTGAGATTAGGAATCCTCAATCTTATACTGGGACAACTT

GCAAACCTGCTCAGCCTTTGTCTCTGATGAAGATATTATCTTCATGATCT

TGGATTGAAAACAGACCTACTCTGGAGGAACATATTGTATCGATTGTCCT

TGACAGTAAACAAATCTGTTGTAAGAGACATTATCTTTATTATCTAGGAC

AGTAAGCAAGCCTGGATCTGAGAGAGATATCATCTTGCAAGGATGCCTGC

TTTACAAACATCCTTGAAACAACAATCCAGAAAAAAAAAGGTGTTGCTGT

CTTTGCTCAGAAGACACACAGATACGTGACAGAACCATGGAGAATTGCCT

CCCAACACTGTTCAGCCAGAGCCTTCCACCCTTGTCTGCAGGACAGTCTC

AACGTTCCACCATTAAATACTTCTTCTGTCACATCCTGCTTATTTATGCC

TAACCAAGGTTCTAGGTCCCGATCGACTGTGTCTGGCAGCACTCCACTGC

CAAACCCAGAATAAGGCAGCGCTCAGGATCCCGAAGGGGCATGGCTGGG

ATCAGAACTTCTGGGTTTGAGTGAGGAGTGGGTCCACCCTCTTGAATTTC

AAAGGAGGAAGAGGCTGGATGTGAAGGAACTGGGGGAGGGAAAGTGTCAG

TTCCGAACTCTTAGGTCAATGAGGGAGGAGACTGGTAAGGTCCCAGCTCC

CGAGGTACTGATGTGGGAATGGCCTAAGAATCTCATATCCTCAGGAAGAA

GGTGCTGGAATCCTGAGGGGTAGAGTTCTGGGTATATTTGTGGCTTAAGG

CTCTTTGGCCCCTGAAGGGCAGAGGCTGGAACCATTAGGTCCAGGGTTTG

GGGTGATAGTAATGGGATCTCTTGATTCCTCAAGAGTCTGAGGATCGAGG
```

```
GTTGCCCATTCTTCCATCTTGCCACCTAATCCTTACTCCACTTGAGGGTA
TCACCAGCCCTTCTAGCTCCATGAAGGTGCCCCTGGGCAAGCACAATCTG
AGCATGAAAGATGCCCCAGAGGCCTTGGGTGTCATCCACTCATCATCCAG
CATCCACACTCTGAGGGTGTGGCCAGCACCATGACGTCATGTTGCTGTGA
CTATCCCTGCAGCGTGCCTCTCCAGCCACCTGCCAACCGTAGAGCTGCCG
ACATCCTCCTCTGGTGGGAGTGGCCTGCATGGTGCCAGGCTGAGGCCTAG
TGTCAGACAGGGAGCCTGGAATCATAGGGATCCAGGACTCAAAGTGCTA
GAGAATGGCCATATGTCACCATCCATGAAATCTCAAGGGCTTCTGGGTGG
AGGGCACAGGGACCTGAACTTATGGGTTTTCCCCAAGTCTATTGCTCTCC
CAAGTGAGTCTCCCAGATACGAGGCACTGTGCCAGCATCAGCCTTATCTC
CACCACATCTTGTAAAAGGGACTACCCAGGGCCCTGATGAACACCATGGT
GTGTACAGGAGTAGGGGGTGGAGGCACGGACTCCTGTGAGGTCACAGCCA
AGGGAGCATCATCATGGGTGGGGAGGAGGCAATGGACAGGCTTGAGAACG
GGGATGTGGTTGTATTTGGTTTTCTTTGGTTAGATAAAGTGCTGGGTATA
GGATTGAGAGTGGAGTATGAAGACCAGTTAGGATGGAGGATCAGATTGGA
GTTGGGTTAGAGATGGGGTAAAATTGTGCTTCGGATGAGTTTGGGATTGA
CACTGTGGAGGTGGTTTGGGATGGCATGGCTTTGGGATGGAAATAGATTT
GTTTTGATGTTGGCTCAGACATCCTTGGGGATTGAACTGGGGATGAAGCT
GGGTTTGATTTTGGAGGTAGAAGACGTGGAAGTAGCTGTCAGATTTGACA
GTGGCCATGAGTTTTGTTTGATGGGGAATCAAACAATGGGGAAGACATA
AGGGTTGGCTTGTTAGGTTAAGTTGCGTTGGGTTGATGGGGTCGGGCTG
TGTATAATGCAGTTGGATTGGTTTGTATTAAATTGGGTTGGGTCAGGTTT
TGGTTGAGGATGAGTTGAGGATATGCTTGGGGACACCGGATCCATGAGGT
TCTCACTGGAGTGGAGACAAACTTCCTTTCCAGGATGAATCCGGGGAAGC
CTTAATTCACGTGTAGGGGAGGTCAGGCCACTGGCTAAGTATATCCTTCC
ACTCCAGCTCTAAGATGGTCTTAAATTGTGATTATCTATATCCACCTCTG
TCTCCCTCACTGTGCTTGGAGTTTACCTGATCACTCAACTAGAAACAGGG
GAAGATTTTATCAAATTCTTTTTTTTTTTTTTTTTTTGAGACAGAG
TCTCACTCTGTTGCCCAGGCTGGAGTGCAGTGGCGCAGTCTCGGCTCACT
GCAACCTCTGCCTCCCAGGTTCAAGTGATTCTCCTGCCTCAGCCTCCTGA
GTTGCTGGGATTACAGGCATGCAGCACCATGCCCAGCTAATTTTTGTATT
TTTAGTAGAGATGGGGTTTCACCAATGTTTGCCAGGCTGGCCTCGAACTC
CTGACCTGGTGATCCACCTGCCTCAGCCTCCCAAAGTGCTGGGATTACAG
GCGTCAGCCACCGCGCCCAGCCACTTTTGTCAAATTCTTGAGACACAGCT
CGGGCTGGATCAAGTGAGCTACTCTGGTTTTATTGAACAGCTGAAATAAC
CAACTTTTTGGAAATTGATGAAATCTTACGGAGTTAACAGTGGAGGTACC
AGGGCTCTTAAGAGTTCCCGATTCTCTTCTGAGACTACAAATTGTGATTT
TGCATGCCACCTTAATCTTTTTTTTTTTTTTTAAATCGAGGTTTCAGT
CTCATTCTATTTCCCAGGCTGGAGTTCAATGGCGTGATCACAGCTCACTG
TAGCCTTGAACTCCTGGCCTTAAGAGATTCTCCTGCTTCGGTCTCCCAAT
AGCTAAGACTACAGTAGTCCACCACCATATCCAGATAATTTTTAAATTTT
```

```
TTGGGGGGCCGGGCACAGTGGCTCACGCCTGTAATCCCAACACCATGGGA
GGCTGAGATGGGTGGATCACGAGGTCAGGAGTTTGAGACCAGCCTGACCA
ACATGGTGAAACTCTGTCTCTACTAAAAAAAAAAAAAATAGAAAAATTAG
CCGGGCGTGGTGGCACACGGCACCTGTAATCCCAGCTACTGAGGAGGCTG
AGGCAGGAGAATCACTTGAACCCAGAAGGCAGAGGTTGCAATGAGCCGAG
ATTGCGCCACTGCACTCCAGCCTGGGTGACAGAGTGAGACTCTGTCTCAA
AAAAAAAAAATTTTTTTTTTTTTTGTAGAGATGGATCTTGCTTTGTTT
CTCTGGTTGGCCTTGAACTCCTGGCTTCAAGTGATCCTCCTACCTTGGCC
TCGGAAAGTGTTGGGATTACAGGCGTGAGCCACCATGACTGACCTGTCGT
TTAATCTTGAGGTACATAAACCTGGCTCCTAAAGGCTAAATATTTTGTTG
GAGAAGGGGCATTGGATTTTGCATGAGGATGATTCTGACCTGGGAGGGCA
GGTCAGCAGGCATCTCTGTTGCACAGATAGAGTGCACAGGTCTGGAGAAC
AAGGAGTGGGGGGTTATTGGAATTCCACATTGTTTGCTGCACGTTGGATT
TTGAAATGCTAGGGAACTTTGGGAGACTCATATTTCTGGGCTAGAGGATC
TGTGGACCACAAGATCTTTTTATGATGACAGTAGCAATGTATCTGTGGAG
CTGGATTCTGGGTTGGGAGTGCAAGGAAAAGAATGTACTAAATGCCAAGA
CATCTATTTCAGGAGCATGAGGAATAAAAGTTCTAGTTTCTGGTCTCAGA
GTGGTGCAGGGATCAGGGAGTCTCACAATCTCCTGAGTGCTGGTGTCTTA
GGGCACACTGGGTCTTGGAGTGCAAAGGATCTAGGCACGTGAGGCTTTGT
ATGAAGAATCGGGGATCGTACCCACCCCCTGTTTCTGTTTCATCCTGGGC
GTGTCTCCTCTGCCTTTGTCCCCTAGATGAAGTCTCCATGAGCTACAGGG
CCTGGTGCATCCAGGGTGATCTAGTAATTGCAGAACAGCAAGTGCTAGCT
CTCCCTCCCCTTCCACAGCTCTGGGTGTGGGAGGGGGTTGTCCAGCCTCC
AGCAGCATGGGGAGGGCCTTGGTCAGCCTCTGGGTGCCAGCAGGGCAGGG
GCGGAGTCCTGGGGAATGAAGGTTTTATAGGGCTCCTGGGGGAGGCTCCC
CAGCCCCAAGCTT
```

A skilled artisan will recognize that other structurally and functionally equivalent promoters can be used in the just-described promoter reporter assays, e.g., promoters that are at least 75% identical to SEQ ID NO:4 (i.e., any percent identity between 75% and 100%). Such promoters should include at least one copy of an androgen-responsive element, e.g., any of SEQ ID NOs:1-3.

Examples of equivalent promoters include those with deletions or additions of up to 40 nucleotides and retaining at least 70% of the promoter activity of SEQ ID NO:4. Uses of such promoters are also within the scope of the claimed invention.

Promoter activity can be quantified by measuring a property of the reporter polypeptide (e.g., enzymatic activity or fluorescence), reporter polypeptide expression (e.g., by an ELISA assay), or reporter mRNA expression (e.g., by a fluorescent hybridization technique). PSA promoter activity is compared between a first group exposed to an agonist of the AR (e.g., testosterone or 5α-dihydrotestosterone) and a test composition and a second group exposed to the AR agonist alone. If reporter activity or expression is increased or decreased in the first group relative to the second group, then the test composition is identified as an IKKαRT modulator.

Suitable reporter polypeptides include, e.g., firefly luciferase, *Renilla* luciferase, fluorescent proteins (e.g., enhanced green fluorescent protein), β-galactosidase, β-lactamase, alkaline phosphatase, and horseradish peroxidase.

For example, luciferase activity can be detected by providing an appropriate luminogenic substrate, e.g., firefly luciferin for firefly luciferase or coelenterazine for *Renilla* luciferase. Luciferase activity in the presence of an appropriate substrate can be quantified by a number of standard techniques, e.g., luminometry.

Reporter activity measurements can be normalized to protein concentration in cell lysates. Protein concentration can be determined, e.g., by a Coomassie assay using commercially available reagents. Alternatively, a second reporter construct, i.e., a "normalization reporter construct," can be used to normalize reporter activity measurements. The normalization reporter polypeptide encoded by the normalization reporter construct generally has an activity that is distinct from that of the above-described androgen-responsive reporter polypeptide. Further, the normalization reporter construct generally includes a weak constitutive promoter, e.g., the herpes thymidine kinase promoter that drives expression of the reporter polypeptide. The normalization reporter construct can be separate from or part of the same nucleic acid that includes the first reporter construct (e.g., as part of one plasmid). Promoter activity can be quantified by taking the ratio of androgen-responsive reporter polypeptide activity to normalization reporter polypeptide activity. For example, in a dual luciferase reporter assay, firefly luciferase can serve as the reporter polypeptide indicative of androgen-responsive promoter activity and *Renilla* luciferase can serve as a normalization reporter polypeptide. Details of the dual luciferase assay, including high-throughput methods, are disclosed in U.S. Pat. No. 5,744,320.

Reporter expression or activity can be assayed in a cell free assay (e.g., a cell lysate) or in live cells, depending on the reporter polypeptides or reporter enzyme substrates selected for the assay. Cell free assays can be conducted in any suitable vessel (e.g., microtiter plates, test tubes, cuvettes, and microcentrifuge tubes). Live cell assays can be conducted in any vessel suitable for mammalian cell culture (e.g., microtiter cell culture plates, multiwell plates, cell culture dishes, and cell culture flasks). Multi-well cell culture plates can be adapted for direct luminometry or fluorimetry of cells or cell lysates in the wells of the plate. Luciferase activity can be measured in live cells by adding a suitable luciferase substrate directly to the cultured cells in cell culture medium (i.e., without a lysis step) and measuring light emission directly from the intact cells. Viviren™ substrate (Promega, Wis.) or other suitable cell-permeable luciferase substrates can be added directly to cells to measure luciferase activity.

Fluorescent polypeptides (e.g., EGFP) can be detected and quantified in live cells by a number of detection methods known in the art (e.g., fluorimetry or fluorescence microscopy). Details of reporter assays screens in live cells using fluorescent polypeptides, including high-throughput methods, can be found, e.g., in U.S. Pat. No. 6,875,578.

Reporter mRNA and protein expression levels can be determined by a number of conventional methods. For example, expression of reporter mRNA from treated and untreated cells can be monitored by standard RNA blot analysis or can be aided by PCR, especially quantitative PCR (qPCR) or similar techniques known in the art (see, e.g., *Current Protocols in Molecular Biology*, John Wiley & Sons, N.Y. (2005), 15.5-15.7). Immunoassays can also be used to detect or monitor reporter polypeptide levels. Specific polyclonal or monoclonal antibodies are commercially available for a number of reporter polypeptides (e.g., EGFP, luciferase, or β-galactosidase) and may be used in any standard immunoassay format. Useful assays for measuring reporter polypeptide levels include competitive and non-competitive assays, radioimmunoassays, bioluminescence and chemiluminescence assays, fluorometric assays, sandwich assay, dot blots, enzyme linked assays (including ELISA), microtiter plates, and antibody coated strips or dipsticks for rapid monitoring of blood. For each method, the range, sensitivity, precision, reliability, specificity and reproducibility of the assay is established. Examples of some immunoassays are described in detail in, e.g., *Current Protocols in Molecular Biology*, John Wiley & Sons, N.Y. (2005), 11.1-11.3.

Optionally, the level AR-regulated IKKα kinase activity can be determined in reporter cells that are exposed to a test composition or a negative control composition (e.g., cell culture medium). For example, following androgen stimulation of cells plus or minus an IKKαRT-modulator test composition, a cell lysate can be prepared and the level of AR-complexed IKKα kinase can be determined by immunoprecipitation using an AR monoclonal antibody, e.g., AR-441 from Santa Cruz Biotechnology, Inc. (Santa Cruz, Calif.) followed by an in vitro protein kinase assay using histone H3 as a substrate. The level of histone H3 phosphorylation indicates the level of AR-stimulated IKKα activity. Alternatively, IKKα activity in the presence of a test composition can be determined in vitro. For example, total IKKα can first be immunoprecipitated from a cell lysate using a polyclonal anti-IKKα polyclonal antibody, available from, e.g., Santa Cruz Biotechnology, Inc. (Santa Cruz, Calif.). The immunoprecipitated kinase is then assayed for its ability to phosphorylate histone H3 in the presence or absence of the test composition.

Androgen-responsive reporter cells as described above, e.g., androgen-responsive reporter cell lines, are also useful for determining IKKαRT activity in a non-human mammalian test subject, e.g., in a mouse, rat, hamster, guinea pig, rabbit, dog, cat, or monkey. Animal models that are tolerant of xenografts, e.g., the nude mouse or the nude rat are particularly useful. Reporter cells are first infused into the test subject. Reporter activity is subsequently assayed in a biological sample obtained from the test subject (e.g., a blood sample, skin sample prostate tissue biopsy sample, etc.) Alternatively or in addition, reporter activity can be detected directly in the test subject, i.e., in vivo. Luciferase is a particularly useful reporter polypeptide for in vivo detection. For example, an appropriate luminogenic substrate (e.g., luciferin) is administered to the test subject containing reporter cells that express luciferase. Photon emissions resulting from in vivo luciferase activity are then detected in vivo, e.g., by optical tomography techniques, as described in, e.g., U.S. Pat. No. 6,596,257 Charge-coupled device cameras useful for in vivo imaging are commercially available, e.g. the IVIS® system from Xenogen (Alameda, Calif.). The level of IKKα activity in a biological sample from the test subject can also be assayed, by the methods described above. The biological sample to be assayed for IKKα activity can include reporter cells only, both reporter cells and native cells, or native cells only.

The measurement of reporter and IKKα activities in a test subject are useful, e.g., in assessing the in vivo effectiveness of IKKαRT modulators identified in the above-described test composition reporter assays.

The promoter reporter assays described above can be used to identify compositions that inhibit IKKαRT. Such compositions include plant extracts, e.g., from *Wedelia chinensis, Eclipta prostrata*, or *Eclipta alba*, and pure compounds), and pure compounds that inhibit IKKα activity, e.g., wedelolactone, luteolin, quercetin, apigenin, 15-deoxy $\Delta^{12,14}$-prostaglandin $J_2$, and prostaglandin A1.

IKKαRT inhibitors can be used to treat an androgen-stimulated disease. For example, a subject in need can be administered a composition containing an effective amount of an IKKαRT inhibitor, e.g., a composition containing an *Eclipta prostrata* extract or wedelolactone, to treat an androgen-stimulated disease, e.g., prostate cancer, benign prostate hypertrophy, breast cancer, male alopecia, propionibacterium acne, polycystic ovarian syndrome, autosomal dominant polycystic kidney disease, or hyperandrogenism. Prior to administration of the inhibitor composition, the subject can be diagnosed as suffering from an androgen-stimulated disease or having a high risk thereof. For example, in the case of prostate cancer, the level of PSA is determined in a biological sample from the subject (e.g., a blood sample). Assays for PSA can be carried out as described in, e.g., U.S. Pat. No. 6,300,088. The measurement of a PSA level can also be carried out at various time points after administration of the inhibitor composition as an indicator of therapeutic response to this treatment.

In some cases, a subject may have a high risk of developing prostate cancer, e.g., as indicated by an excessively high PSA level. Accordingly, the subject's risk of prostate cancer can be reduced by prophylactically administering to the subject a composition containing an effective amount of an IKKαRT inhibitor.

The above-mentioned inhibitor compositions including plant extracts, e.g., from *Wedelia chinensis, Eclipta prostrata*, or *Eclipta alba*, and pure compounds, e.g., wedelolactone, luteolin, quercetin, apigenin, 15-deoxy $\Delta^{12,14}$ prostaglandin $J_2$, or prostaglandin A1, can be incorporated into pharmaceutical compositions for prophylactic or therapeutic use. For example, a pharmaceutical composition can include an effective amount of wedelolactone and a pharmaceutically acceptable carrier. The term "an effective amount" refers to the amount of an active composition that is required to confer a prophylactic or therapeutic effect on the treated subject. Effective doses will vary, as recognized by those skilled in the art, depending on the types of diseases treated, the severity of the diseases, the general health and/or age of the subject, previous treatments, route of administration, excipient usage, and the possibility of co-usage with other prophylactic or therapeutic treatment.

To practice the method of the present invention, an active composition can be administered parenterally, orally, nasally, rectally, topically, or buccally. The term "parenteral" as used herein refers to subcutaneous, intracutaneous, intravenous, intramuscular, intra-articular, intra-arterial, intrasynovial, intrasternal, intrathecal, or intralesional, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

An active composition can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Generation and Characterization of a Prostate Cancer Reporter Cell Line

The 22Rv1 cell line was purchased from ATCC. Reporter plasmid (p5.7 kb-PSA-Luc) was constructed by inserting the 5.7 kb PSA promoter into pGL3 plasmid (Promega). The 22RvPSA36-103 cell line was derived by stable transfection of p5.7 kb-PSA-Luc and pGK-puro into 22Rv1 cells and selected against puromycin as described (Fryer and Archer, 1998).

For luciferase activity assays, $8 \times 10^4$ 22Rv1-derived cells were grown in 48-well multi-well plates. The cell culture medium was RPMI containing 5% charcoal coated dextran stripped fetal bovine serum (Hyclone). After the cells were grown for one day in culture, their growth medium was exchanged to include experimental or control compositions, as described below, and cell growth was continued for a further 20 hours. Cells were lysed by the addition of passive lysis buffer (Promega), then luciferase assays were performed using a luciferase assay system (Promega) and VICTOR$^2$ multilabel counter (PerkinElmer), and normalized to lysate protein as measured by a Coomassie (Bradford) Protein Assay Kit (Pierce).

The AR signaling pathway promotes the development of prostate cancer. Thus, we established a cell-based model to observe androgen-responsive promoter activity in human prostate cancer cells. We stably transfected a PSA-luciferase reporter into 22Rv1 cells to generate the 22RvPSA36-103 androgen-responsive reporter cell line. 22RvPSA36-103 cells were incubated for 20 hours in the presence of an androgen. PSA-luciferase activity was stimulated in a dose dependent manner by the androgens, testosterone or 5α-dihydrotestosterone (10 nM) up to approximately 100 fold over baseline. Induction of PSA-luciferase expression in 22RvPSA36-103 cells was specific to androgens, as the steroid hormones 17-β-estradiol and progesterone failed to induce PSA-luciferase expression, similar to the steroid specificity of CWR22 xenografts in vivo as in Shao et al., (2003), *Prostate*, 57:1-7. The low basal activity and effective induction of PSA-luciferase expression by androgens demonstrated that 22RvPSA36-103 cells could be used to identify modulators of androgen-responsive promoter activity.

Example 2

Androgen Induces AR Interaction with IKKα

We investigated if IKKα or IKKβ could interact with activated AR in 22Rv/PSA36-103 cells after androgen stimulation. Co-immunoprecipitation of the AR in a complex with IKKα was detected after exposing the cells to 10 nM 5α dihydrotestosterone for five minutes. The level of AR-associated IKKα accumulated and peaked from 10 to 15 minutes, then declined after 30 minutes, and completely diminished after 60 minutes. In contrast, at all time points IKKβ was only detected at very low levels in AR complex. The AR and IKKα were co-localized in the nucleus as determined by indirect immunofluorescence staining using AR and IKKα antibodies. Their co-localization followed a time course similar to that determined by co-immunoprecipitation of these proteins.

Together, these results demonstrated that AR activation induced the formation of a complex between AR and IKKα in the cell nucleus to activate androgen-responsive target gene transcription.

Example 3

IKKα Inhibition Reduces Androgen-Responsive Promoter Activity

The ability of the IKK inhibitors 15-deoxy-$\Delta^{12,14}$-prostaglandin $J_2$, prostaglandin A1, and wedelolactone to inhibit androgen-responsive promoter activity was tested using the above-described luciferase assay. These compounds inhibited 5α-dihydrotestosterone-induced luciferase expression in a dose-dependent manner. In contrast, the IKK-β-specific inhibitor SC-514 exerted no effect on androgen-responsive promoter activity at any of the concentrations tested. This result suggested that the AR-signaling pathway acts specifically through IKKα.

To confirm this conclusion, we constructed 22RvPSA36-103 cell lines capable of inducible RNAi-knockdown of IKKα or IKKβ.

The small hairpin RNAi expression system we used was a modification of the inducible expression system reported elsewhere (van de Wetering et al., 2003). The following hairpin knockdown sequences were used:

IKKα (sense 5'-GCAGGCUCUUUCAGGGACA-3') (SEQ ID NO: 5)

IKKβ (sense 5'-GGUGAAGAGGUGGUGUGAGC-3') (SEQ ID NO: 6)

Both sequences were reported in Takaesu et al., 2003. A tet operon-regulated H1-small hairpin RNA expression cassette was constructed and inserted into the pcDNA6tTR™ plasmid from Invitrogen (Carlsbad, Calif.). Each knockdown plasmid was transfected into 22RvPSA36-103 cells to produce stably transfected cell lines. The knockdown of IKKα or IKKβ in daughter cell lines was determined by immunoblotting. The two cell clones showing the most significant knockdown were used for further studies. To induce RNAi-mediated knockdown, cells were grown in medium containing 1 μg/ml doxycycline as compared to vehicle control for 3 days. Subsequent treatment and assays were performed according to the procedure of the aforementioned luciferase assays.

Consistent with the above-described IKK inhibitor results, RNAi knockdown of IKKα decreased androgen-induced PSA-luciferase expression by 50% to 60%. In contrast, knockdown of IKKβ showed no effect on luciferase induction by androgen, suggesting that IKKα but not IKKβ is required for androgen-responsive promoter activity.

Example 4

Effect of IKKα Inhibitors on Prostate Cancer Cell Growth

Given that activation of the AR signaling pathway stimulates prostate cancer cell proliferation and our finding that IKKα is implicated in this pathway, we sought to determine if IKKα inhibition would reduce prostate cancer cell proliferation. To this end, the colony forming efficiency of 22Rv1 cells and 22RvPSA36-103 cells in the presence of an androgen plus or minus an IKK inhibitor was determined by growing $2 \times 10^4$ cells in 12-well multi-well plates for 6 days. The growth medium was replaced every three days. At the end of the growth period, cell colonies were stained with 0.1% crystal violet in phosphate buffer saline, dried, and photographed. Cellular retention of crystal violet was extracted with 20% acetic acid in water and measured at $OD_{595}$ as a quantitative indicator of colony forming efficiency.

Wedelolactone, at the same concentrations that were used in the above experiments to inhibit androgen-responsive promoter activity, proved highly effective in inhibiting androgen-stimulated colony growth of both 22Rv1 and 22RvPSA36-103 cells in a dose-dependent manner. In contrast, the IKKβ-specific inhibitor SC-514 failed to inhibit colony growth. RNAi knockdown of IKKα was also effective in reducing androgen-stimulated colony growth. On the other hand, RNAi knockdown of IKKβ failed to reduce colony growth.

These results established that IKKα is critical to androgen-stimulated cell proliferation as it occurs in prostate cancer, and that inhibition of IKKα can be an effective treatment for this cancer.

Other Embodiments

All of the features disclosed in this specification may be combined in any combination. Each feature disclosed in this specification may be replaced by an alternative feature serving the same, equivalent, or similar purpose. For example, the ability of a candidate IKKαRT modulator composition to inhibit IKKα activity can be assayed from IKKα-expressing cells other than androgen-responsive reporter cells. Indeed, such assays are also within the scope of the invention.

From the above description, one skilled in the art can easily ascertain the essential characteristics of the present invention, and without departing from the spirit and scope thereof, can make various changes and modifications of the invention to adapt it to various usages and conditions. Thus, other embodiments are also contemplated.

What is claimed is:

1. A method of treating benign prostate hypertrophy in a subject in need thereof, comprising administering to the subject an effective amount of a composition containing a *Wedelia chinesis* extract.

2. The method of claim 1, further comprising, prior to the administering step, diagnosing the subject as having benign prostate hypertrophy.

3. The method of claim 1, wherein the composition is administered orally.

* * * * *